(12) United States Patent
Sohn et al.

(10) Patent No.: US 6,444,805 B1
(45) Date of Patent: Sep. 3, 2002

(54) RECOMBINANT HUMAN PAPILLOMAVIRUS VACCINE EXPRESSED IN TRANSGENIC PLANTS

(75) Inventors: Ulk Sohn, Taegu; Hong Gil Nam, Pohang; Deok Hoon Park, Pohang; Kuk Hyun Kim, Pohang, all of (KR)

(73) Assignee: Genomine, Inc., Pohang (KR)

( * ) Notice: Subject to any disclaimer, the term of this patent is extended or adjusted under 35 U.S.C. 154(b) by 0 days.

(21) Appl. No.: 09/512,569

(22) Filed: Feb. 24, 2000

(30) Foreign Application Priority Data

Feb. 15, 2000 (KR) .......................................... 2000-7022

(51) Int. Cl.⁷ .......................... C07H 21/04; A61K 39/12
(52) U.S. Cl. .................................. 536/23.72; 424/204.1
(58) Field of Search ..................... 424/204.1; 536/23.72

(56) References Cited

U.S. PATENT DOCUMENTS 5,861,277 A * 1/1999 Rose et al. .................. 435/69.1

OTHER PUBLICATIONS

Jiang, Xi et al. "Expression, Self–Assembly, and Antigenicity of the Norwalk Virus Capsid Protein," *J. of Virology* 66(11): 6527–32 (1992).

Mason, Hugh S. et al. "Expression of Norwalk virus capsid protein in transgenic tobacco and potato and its oral immunogenicity in mice," *Proc. Natl. Acad. Sci. USA* 93:5335–40 (1996).

Rose, Robert C. et al. "Oral vaccination of mice with human papillomavirus virus–like particles induces systemic virus–neutralizing antibodies," *Vaccine* 17:2129–35 (1999).

Thanavala, Y. et al. "Immunogenicity of transgenic plant–derived hepatitis B surface antigen," *Proc. Natl. Acad. Sci. USA* 92:3358–61 (1995).

* cited by examiner

*Primary Examiner*—Hankyel T. Park
(74) *Attorney, Agent, or Firm*—Lahive & Cockfield, LLP; Jane E. Remillard, Esq.; Richa Nand, Esq.

(57) ABSTRACT

The oral vaccine of the present invention containing the HPV like particles is produced in edible transgenic plants and then administered through the consumption of the edible portion of those plants or after the purification of the particles. A DNA sequence encoding one of the HPV capsid proteins is isolated, inserted into the plasmid which comprises a plant-specific promoter and a gene for a selection marker, and then transferred to plant cells to give transgenic plants. Since the gene is expressed in a portion of the plants, the oral vaccine of the present invention can be produced in an inexpensive manner and administered in a simple method.

7 Claims, 9 Drawing Sheets

RECOMBINANT HUMAN PAPILLOMAVIRUS VACCINE EXPRESSED IN TRANSGENIC PLANTS

BACKGROUND OF THE INVENTION

The present invention relates to vaccines, more particularly, to the production of oral vaccines in transgenic edible plants which can produce human papillomavirus (hereinafter, abbreviated 'HPV') like particles.

Papillomavirus, a genus of Papovaviridae, is a double strand DNA tumor virus infecting mammals such as deer, dog, goat, horse, rat and sheep as well as human (Pfister, H., 1987, *Adv. Cancer Res.*, 48, 113–147). The virus infects the basal cells of the epidermis or mucosa of the host to induce papillomas commonly known as warts or verrucas.

About twenty types of the known seventy types of HPV induce benign tumours and involve in development of malignant tumours in the mucosal epithelium of a mouth or a genital tract (Zur Hausen H., 1988, *Mol Carcinogenesis* 8:147–150). Especially the type of HPV-16 or HPV-18 is the main cause of the cancer of genital tract, particularly of the cervix, which is one of the commonest woman's cancers, while the HPV-18 is more closely related to the malignancy (Rends M. J., Donaldson Y. K., Duvall E. and Colin C. Bird, 1993, *Human Pathology* 24: 432–437). In the most cases of Korean women, HPV-16, HPV-18, HPV-31, HPV-33 and HPV-35 are found in the diseased cervix tissues.

According to the World Health Organization, cancers of the cervix have been plagued on five hundred thousand or more women around the world every year and particularly in the less developed countries the cancer of cervix is the main cause of women deaths. In Korea, even though the ratio of the subject suffering from the cancer of cervix to total women has been decreased to 22% from 27.7% of a decade ago, the cancer of cervix is still one of the most spread diseases in women.

The cervical cancer occurs in the anogenital region and is transmitted by sexual contact. Untill now, pap smear, cervicography, papilloma virus detection, colposcopy or in situ hybridization method has been used for diagnosis thereof (Lee, Sang-Sook et al., *Korean Met. Association J.*, 33(1): 89–97). However, since most of said diagnostic methods have shortcomings of displeasure and inaccuracy, a simple diagnostic method such as the method of using an antigen-antibody reaction has been required. Moreover, mass-production or recovery method of using animal cell culture system should be developed for the vaccines to be manufactured.

However, the virions can be produced only in the non-dividing, differentiated keratinocytes and these cells cannot be grown in culture, which has made it difficult to produce the virus particles sufficient to molecular biological studies as well as to develop the preventive or curing vaccines. In addition, since HPV is host-specific, there are also many difficulties in developing the animal model system for testing the efficacy of HPV as a vaccine.

Researches for the vaccine for the cervical cancer are focused on a prophylactic and a therapeutic vaccine. Prophylactic vaccines induce the production of neutralizing antibodies against HPV L1/L2 so that they can prevent the infection of the HPV or further progress of the disease to malignant tumour even when the hosts have been already infected. While the therapeutic vaccines targeting HPV E6/E7 induce a humoral immune response to induce the regression of the lesions or malignant tumour cells.

Up to the present, a part of the HPV capsid proteins produced by recombinant DNA techniques and synthetic peptides have been developed as vaccines for the cancer of cervix. Said recombinant proteins were produced in an established systems such as bacteria, yeasts, baculoviruses and recombinant vaccinia viruses, and they are used as tools for detecting the antibodies in serum, which indicates the ability to induce the humoral or cellular immunity.

Hagensee et al. disclosed a method for producing HPV L1 virus like particles (hereinafter, abbreviated 'VLPs') as live recombinant vaccinia viruses in the culture of mammary cells (Hagensee M. E., Yaegashi N., Galloway D. A., 1993, *J. Virol.* 67: 315–322). Gao et al. reported that the formation of tumours was inhibited or delayed in the mice immunized with a HPV E6/E7 protein which was produced by said system (Gao L., Chain B., Sinclair C., 1994, *J Gen. Viol.* 75: 157–164; Meneguzzi G., Cern C., Kieny M. P., 1991, *Virology* 181: 62–69).

A live recombinant vaccinia virus, however, has a disadvantage in that the probability of random mutation causing the production of replicative compatible viruses is too high like other cases, which requires long-term and expensive clinical trials for practical use. To overcome these problems, viruses whose ability to replicate is defective have been developed but there are no available vaccines yet (Moss B., 1996, *Pro. Natl. Acad. Sci.* USA, 93: 11341–11348).

Among other researches for vaccines using a bacterial vector, Denis reported that HPV 16 VLPs produced by attenuated *Salmonella typhimurium* could elicit the production of mucosal or systemic antibodies specific to antigen (Denis, Nardelihaefliger, Richard B. S., Roden, 1997, *Infection and immunity* 65: 3328–3336). The principle of the use of synthetic peptides as a vaccine is based on the vaccination with only the epitopes necessary for the induction of immune response, e.g., in the HPV 16 E6/E7 an epitope inducing a cytotoxic T lymphocyte-mediated response is disclosed (Ressing M. E., Sette A., Brandt R. M., 1995, *J. Immunol.* 154: 5934–5943).

However, there are some difficulties in getting the recombinant protein having a proper antigenicity as a vaccine, due to the fact that said protein produced in a prokaryotic expression system such as *E. coli* does not have a native conformation. It is supported by the report that HPV produced in *E. coli* cannot stimulate cytotoxic T lymphocytes but the production of the antibodies (Cason J., Khan S. A. and Best J. M., 1994, *Vaccine* 11: 603–611).

In order to make the protein have much similarity to the conformation of native protein, animal cells can be used as an expression system of the protein but there are still other problems such as susceptibility to contamination, difficulty in purification, and high cost.

In view of aforementioned reasons, vegetables such as tomato and potato transformed with the vectors carrying the gene encoding an antigenic protein are used to produce a virus itself or parts thereof in the native conformation as an antigen, recently. Said transgenic plant itself may be used as an oral vaccine or an edible vaccine.

As an example of recent advances in the above-mentioned field, surface antigen particle of hepatitis B virus (Thalvala Y. F. and C. J. Artzen, 1995, *Pro. Natl. Acad Sci.* USA 92: 3358–3361) or Norwalk virus like particle (Xi Jiang, Min Wang, David Y. Granham, Mary M. Estes, 1992, *J. Virol.* 66(11), 6527–6532; Mason H. S., Ball J. M., Artzen C. J., 1996, *Pro. Natl. Acad. Sci.* USA 93: 5335–5340) was produced in transgenic plants.

Plant transformation for producing viruses has many advantages in cost, safety and availability. Since the infection of HPV takes place in mucosal surface, oral vaccines may be more effective for the induction of a mucosal immunity than parenteral vaccines.

In addition, oral vaccines produced in edible transgenic plants have other advantages in that delivery, storage, and administration thereof are achieved in inexpensive and simple manner as well as the low production cost and high safety. Particularly, the selling price of the edible vaccine may be lowered to such a low level that it can be easily purchased even in less developed countries.

In view of the efforts to produce an oral vaccine for the cancer of cervix, which is inexpensive and easy to be administered, the inventors completed this invention whereby the transgenic plants producing HPV like particles are provided. Also it is ascertained that said VLPs have efficacy in inducing the production of antibodies by the oral administration as well as the intraperitoneal administration.

SUMMARY OF THE INVENTION

Recombinant viral antigens, anti-viral vaccines and transgenic plants expressing the same are provided by the present invention.

Also a method for producing said vaccines in transgenic plant and an expression vector used for transforming the plant, which comprises a DNA sequence encoding an HPV capsid protein operably linked to a plant-specific promoter and a gene encoding a selection marker, are provided by the present invention.

More particularly, the present invention provides prophylactic or therapeutic vaccines for the cancer of cervix comprising HPV like particles as a pharmaceutically active ingredient.

In accordance with the present invention, some of disadvantages of the prior arts are overcome by providing antigens produced in edible transgenic plants which antigens are antigenically and physically similar to those currently used in the manufacture of anti-viral vaccines derived from human serum or recombinant yeasts.

Other advantages made by the present invention are convenience of administration, possibility of mass-production, ability to elicit a mucosal immunity as well as a systemic immunity, low cost for production of vaccine and no need for those skilled in vaccination. All of that is attributed to the fact that the antigens are produced by edible plant.

The vaccines of the present invention are provided in the forms of injection solution, orally administrable formulation, spray or patch for preventing or curing the cancer of cervix. Further, diagnostic kits comprising said HPV like particles as antigens plus antibodies thereof are included in the scopes of the present invention.

A: pUS-16 L1 vector
B: pUS-16 L2 vector
C: pUS-18 L1 vector
D: pUS-18 L2 vector

Figure 4A:
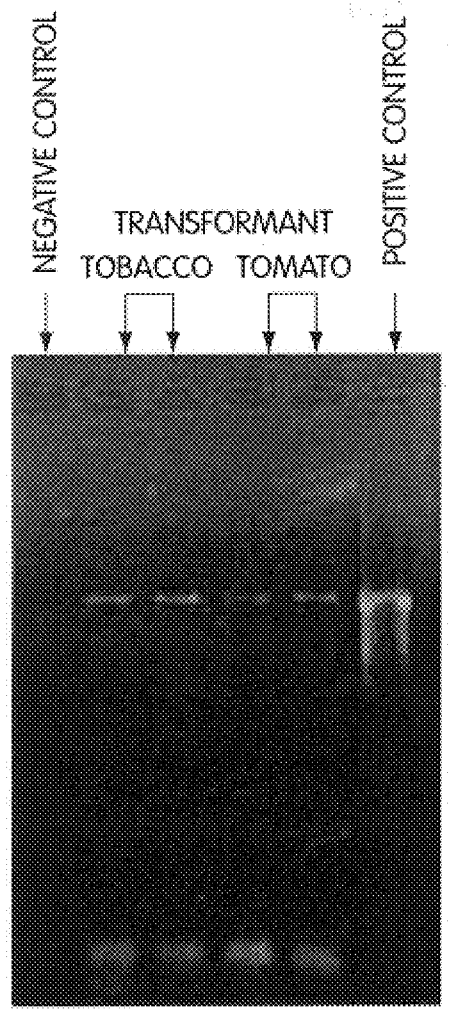
Figure 4B:
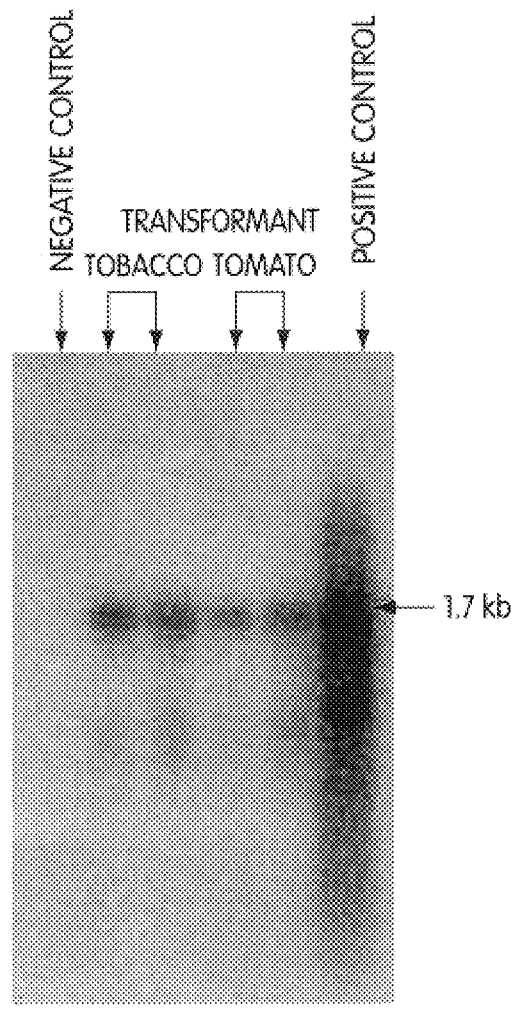
Figure 5A:
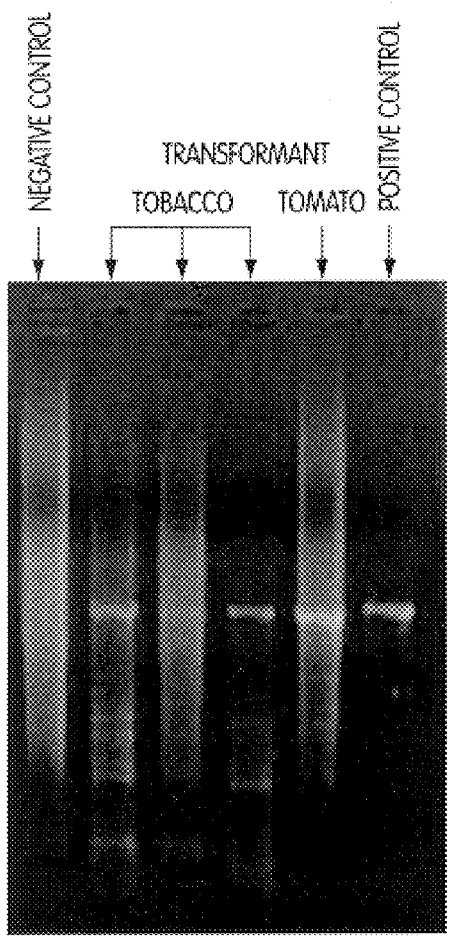
Figure 5B:
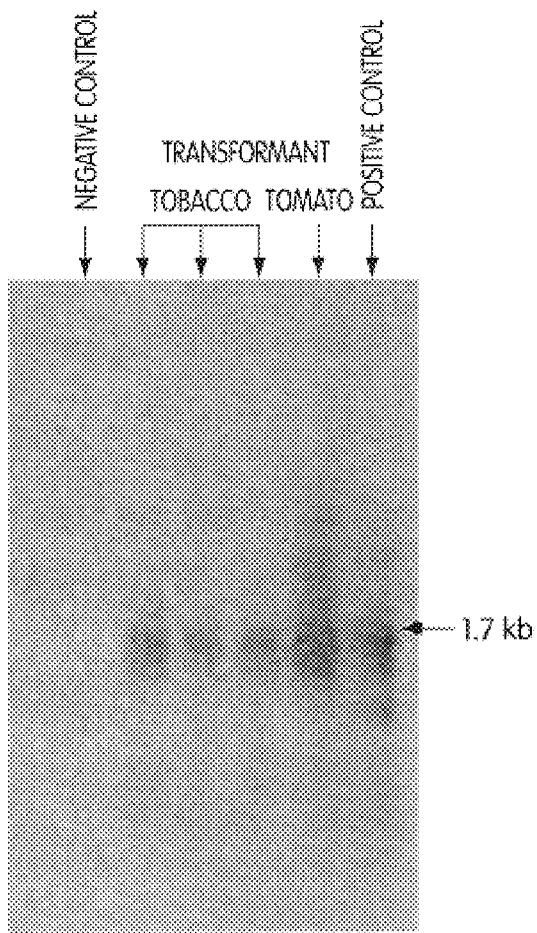
Figure 6A:
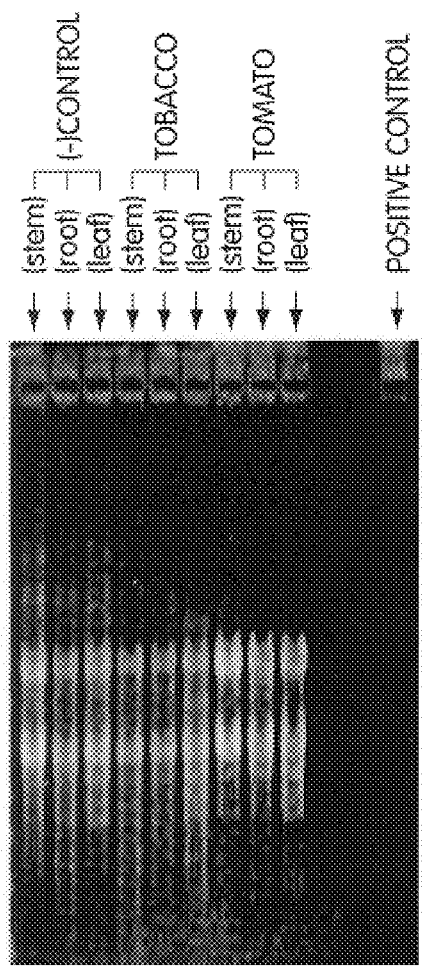
Figure 6B:
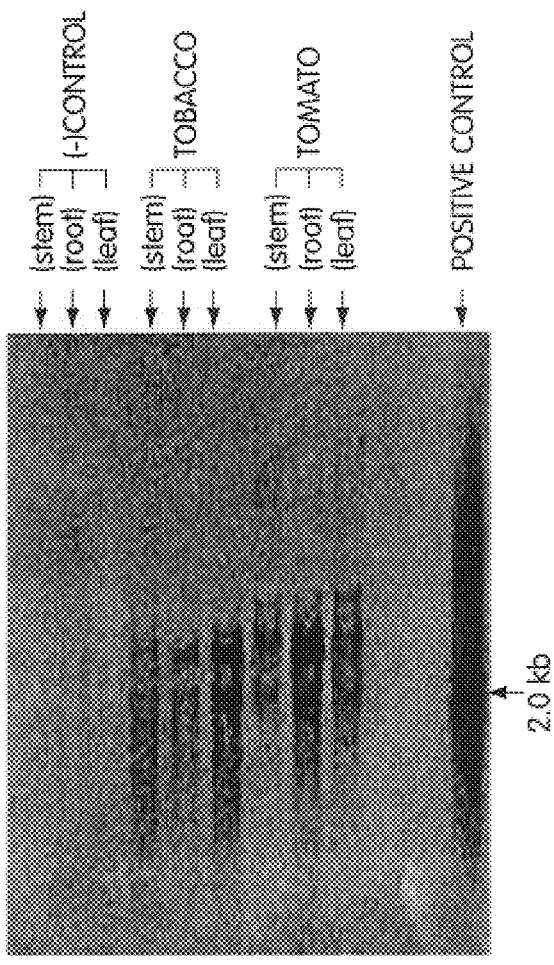
Figure 7A:
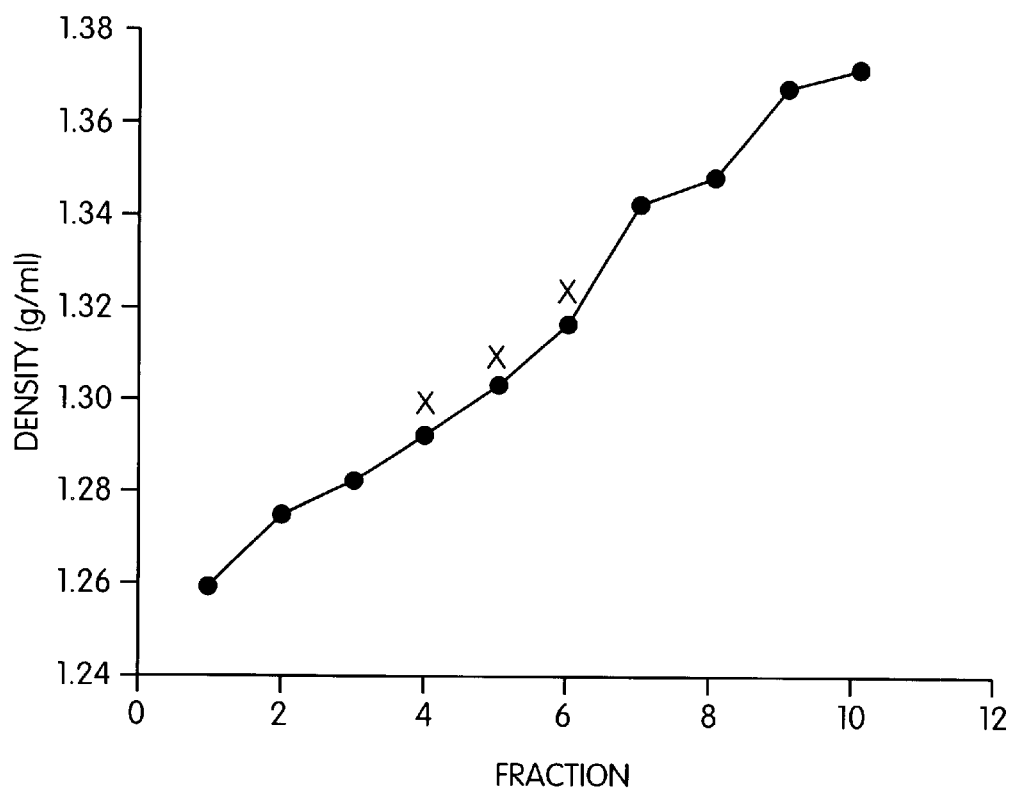
Figure 7B:
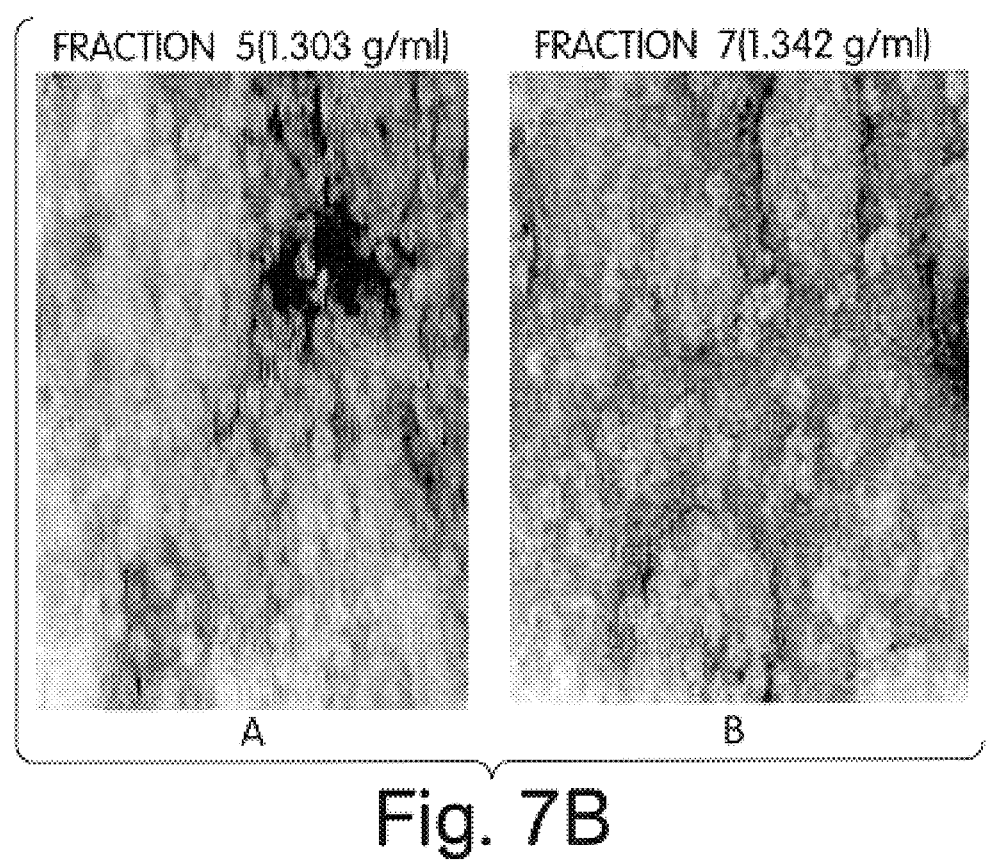
Figure 8:
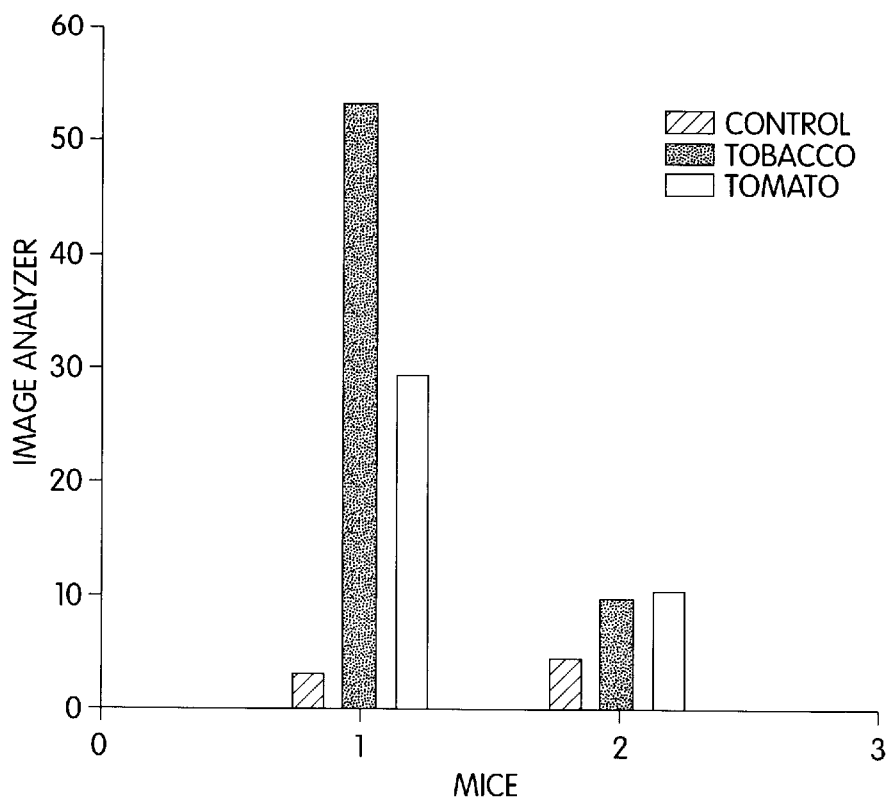
Figure 9:
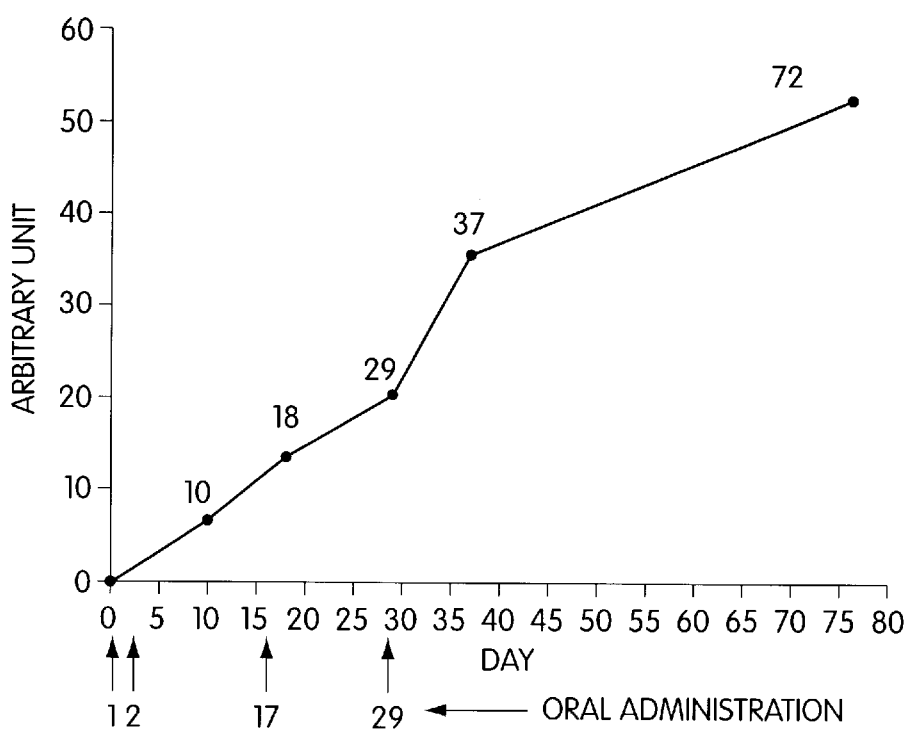
Figure 10:
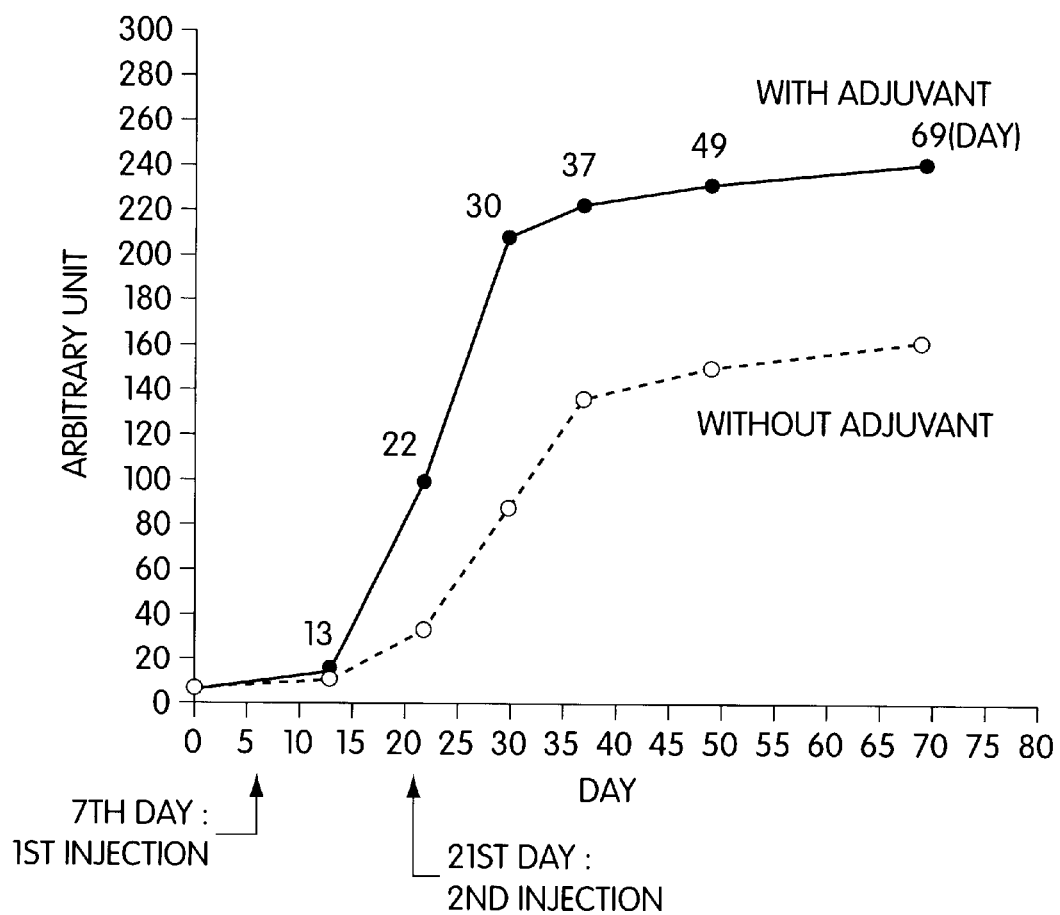

FIG. 4 shows the result of polymerase chain reaction (A) and southern blot (B) with the genomic DNA of the second generation of the transgenic plants (tobacco and tomato);

FIG. 5 shows the result of RT-PCR (A) and southern blot (B) with the genomic DNA of the second generation of the transgenic plants;

FIG. 6 shows the result of northern blot with the genomic DNA of the second generation of the transgenic plants;

A: gel electrophoresis of total RNA
B : autoradiogram of the gel after hydridization FIG. 7a is a graph which shows the fraction containing HPV like particles (depicted as X) fractionated according to the density by CsCl ultracentrifugation;

FIG. 7b is a TEM photograph of VLPs isolated from the transgenic plants by CsCl ultracentrifugation;

FIG. 8 is a graph that illustrates the change of the fecal IgA level after the oral administration of HPV like particles;

FIG. 9 is a graph which illustrates the change of the systemic IgG level after the oral administration of HPV like particles; and FIG. 10 is a graph which illustrates the change of the IgG level in serum after the intraperitoneal injection of HPV like particles;

DETAILED DESCRIPTION OF THE INVENTION

The method of the present invention for producing an antigenic composition includes the steps of:

1) constructing a plasmid vector comprising a DNA sequence encoding an HPV capsid protein operably linked to a plant-specific promoter and a gene encoding a selection marker;

2) transforming a plant tissue with the plasmid vector of step 1;

3) inducing a callus formation from the transformed plant tissue of step 2;

4) inducing a root formation in root-inducing medium, adjusting to soil, and regenerating a transgenic plant; and 5) recovering the HPV like particles from the transgenic plant.

Preferably, the DNA sequence encoding an HPV capsid protein is a DNA sequence encoding a HPV surface antigen, more preferably HPV-16 L1, HPV-16 L2, HPV-18 L1 or HPV-18 L2. But the available DNA sequence is not limited to the said DNA sequences. Said DNA sequence is acquired by amplification method such as a well-known polymerase chain reaction of a gene encoding a component of the HPV isolated in a patient suffering from the cancer of cervix.

A recombinant plasmid vector carrying the said gene is based on a conventional vector expressed in plant, e.g., an ordinary binary vector, a cointegration vector or a vector designed to express in plant without T-DNA region. As for a binary vector, it is preferred to use a vector whose genome comprises a plant-specific promoter and a poly-adenylation signal flanked by two 25 bp repeat sequences found at left and right borders of T-DNA which plays a role in the infection and the integration of Ti plasmid. Further the binary vector contains additionally a gene for a selection marker such as a kanamycin-resistance gene.

In a preferred embodiment of the present invention, the binary vector system is pUS-L series which comprise dual cauliflower mosaic virus 35S promoters (hereinafter, abbreviated 'CaMV 35S') for the high expression in plants, TEV (tobacco etch virus) 5' untranslated leader sequence, a DNA sequence encoding a component of HPV, 35S transcript termination sequence, and polyadenylation signal in due order. More particularly, pUS-18 L1 wherein said DNA sequence encoding a component of HPV is a gene for HPV-18 L1 is deposited in the International Organization for Deposit of Microorganism under the Treaty of Budapest, KRIBB (Taejon-si, Korea), on Feb. 3, 2000 (accession number: KCTC 0729BP).

When the binary vector or cointegration vector is used for transfomation, those skilled in the art should recognize that there are multiple choices of Agrobacterium strains. It is apparent that *A. rhyzogenes* as well as *A. tumefaciens* is suitable according to the object of the application.

If the vector which does not contain a T-DNA segment is used, a method of electroporation, microparticle bombardment, polyethylene glycol mediated uptake or microinjection is an alternative choice for transformation.

In the step 3 of said method for producing an antigenic composition, it is necessary to prepare sterile samples of segments of the plant before cocultivation. For this purpose, seeds are sterilized in ethanol followed by sodium chloride solution, washed, and cultured in Murashige Skook salts medium to germinate. Then the tabacco having 6 leaves or tomato of which real leaves are not formed yet is used for transformation in a preferred embodiment of the present invention.

Plants which are suitable for the practice of the present invention include any dicotyledonous plant and monocotyledonous plant which is edible in part or as a whole such as, but not limited to, tomato, lettuce, white rape, banana, potato, rice, radish, carrot, apple, soybean, corn, berries and other edible varieties. If the transformation method thereof is established well, unicellular algae such as chlorellas which are edible and have chloroplast are also suitable for the practice of the present invention.

As a gene encoding a selection marker, choices can be made in an antibiotic-resistance gene, a herbicide-resistance gene, a metabolic pathway-related gene, a gene relating to the physical properties, a gene encoding a luciferase, a gene encoding a β-glucuronidase(GUS) or a gene encoding a β-galactosidase, etc.

When a small amount of NAA is added to the root-inducing medium, the rooting is completed about 1 week earlier than the case of non-treatment (about 15 days). Therefore, a plant hormone such as NAA, Gamborg's vitamin solution and indole acetic acid is preferably used for root-inducing.

In another preferred embodiment of the present invention, tobacco is used to detect the expression of the gene encoding a HPV component because tobacco is a plant whose transformation method is well established. Tomato was used to validate the possibility of utilizing the system of the present invention as a method for production of oral vaccines.

The calli formed from the transgenic plant cells were induced to root and transferred to a pot to regenerate a whole transgenic plant. In order to confirm whether the transgenic plant has a gene segment of HPV integrated into the plant genome, DNA is isolated, amplified by PCR and examined by genomic southern blotting.

Whether the integrated DNA is transcribed into RNA properly is investigated by reverse transcription-PCR and Northern blotting. The established transgenic plant is grown in green house to give a mature plant, whereby the seeds of the transgenic plant are harvested.

Said Seeds are cultured in a suitable selection medium, resulting in a second generation of the transgenic plant. Ultracentrifugation in cesium chloride shows that the second generation of the transgenic plants can produce antigenic HPV like particles. The principles of CsCl centrifugation are based on the fact that HPV like particles expressed from the foreign DNA show different banding patterns from those of the peculiar protein of the plant.

The isolated HPV like particles are identical or similar to the native conformation of HPV, which was investigated by Western blot using antibodies against HPV of native conformation. Therefore, the resulting HPV like particles have an antigenic property which allows these particles can be used as a prophylactic or therapeutic vaccine in the forms of formulation for oral administration, injection solution, spray or patch and as a component of diagnostic kit.

The oral vaccines produced by the present invention can be administrated by the consumption of the foodstuff that has been manufactured with the transgenic plant producing the antigenic HPV like particles. The edible part of the plant is used as a dietary component while the vaccine is administrated in the process.

To evaluate the antigenecity of the HPV like particles, the level of immunoglobulin A in feces or immunoglobulin G in serum is measured, respectively, after test animals has been immunized with the HPV like particles of the present invention by oral administration or peritoneal injection. The ability to elicit the antibody formation is measured by Enzyme-linked immunosorbent assay. In addition, the direct consumption of the transgenic plant producing the antigenic HPV like particles induces the formation of antibodies against HPV in a host.

The vaccines of the present invention may be formulated with a pharmaceutical vehicle or diluent for oral, intravenous, subcutaneous, intranasal, intrabronchial or rectal administration. The pharmaceutical composition can be formulated in a classical manner using solid or liquid vehicles, diluents and additives appropriate to the desired mode of administration. Orally, the composition can be administered in the form of tablets, capsules, granules, powders and the like with at least one vehicle, e.g., starch, calcium carbonate, sucrose, lactose, gelatin, etc. The preparation may also be emulsified. The active immunogenic ingredient is often mixed with excipients which are pharmaceutically acceptable and compatible with the active ingredient. Suitable excipients are, e.g., water, saline, dextrose, glycerol, ethanol or the like and combination thereof. In addition, if desired, the vaccine may contain minor amounts of auxiliary substances such as wetting or emulsifying agents, pH buffering agents, or adjuvants which enhance the effectiveness of the vaccines. The preparation for parental administration includes sterilized water, suspension, emulsion, and suppositories. For the emulsifying agents, propylene glycol, polyethylene glycol, olive oil, ethyloleate, etc. may be used. For suppositories, traditional binders and carriers may include polyalkene glycol, triglyceride, witepsol, macrogol, tween 61, cocoa butter, glycerogelatin, etc. In addition, pharmaceutical grades of mannitol, lactose, starch, magnesium stearate, sodium saccharine, cellulose, magnesium carbonate and the like can be used as excipients.

More preferably, the HPV like particles of the present invention may be administered by the consumption of the foodstuff that has been manufactured with the transgenic plant and the edible part of the plant is used directly as a dietary component while the vaccine is administrated in the process.

It is preferable to prepare the formulation of the vaccine with the juice of the transgenic plants for the convenience of administration. For said purpose, the plants to be transformed are preferably selected from the edible plants consisting of tomato, carrot and apple, which are consumed usually in the form of juice.

The vaccination will normally be taken at from two to twelve week intervals, more usually from three to hive week intervals. Periodic boosters at intervals of 1–5 years, usually three years, will be desirable to maintain protective levels of the antibodies. It will be desirable to have administrations of the vaccine in a dosage range of the active ingredients of about 100–500 μg/kg, preferably 200–400 μg/kg.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1
Cloning of a DNA Sequence Encoding an HPV Component and Construction of Expression Vector Thereof A. Cloning of a gene encoding an HPV component Polymerase chain reaction was performed to amplify a DNA sequence encoding HPV-18 L1 using the genomic DNA of HPV-18 isolated from a 53-year-old patient in the obstetrics and gynecology of Kyungbuk University in Korea. Two synthetic oligonucleotides (Bioneer, Korea), Sac I tagged oligonucleotide whose nucleotide sequence is SEQ ID NO:1 and Sma I tagged oligonucleotide whose nucleotide sequence is SEQ ID NO:2 were used as a sense primer and a antisense primer, respectively. Oligonucleotides of SEQ ID NO:3 and SEQ ID NO:4 were used as primers for PCR of the DNA encoding HPV-18 L2.

DNA sequences encoding HPV-16 L1 and HPV-16 L2 were obtained from a 45-year-old patient having the cancer of cervix in the same hospital. For the amplification of the DNA encoding HPV-16 L1, oligonucleotides of SEQ ID NO:5 and SEQ ID NO:6 were used as PCR primers, and for the amplification of the DNA encoding HPV-16 L2, oligonucleotides of SEQ ID NO:7 and SEQ ID NO:8 were used.

The used primers were presented in the table 1 below.

18 L1. The amplified genes were digested with Sac I and Sma I, and then the Sac I-Sma I fragments were ligated with an intermediate vector pRTL2 pre-treated with same enzymes. The resultant was designated as pRTL2–18 L1. By the same method, pRTL2–16 L1, pRTL2–16 L2 and pRTL2–18 L2 were constructed and the above four plasmids were designated as pRTL2-L series.

Figure 2:
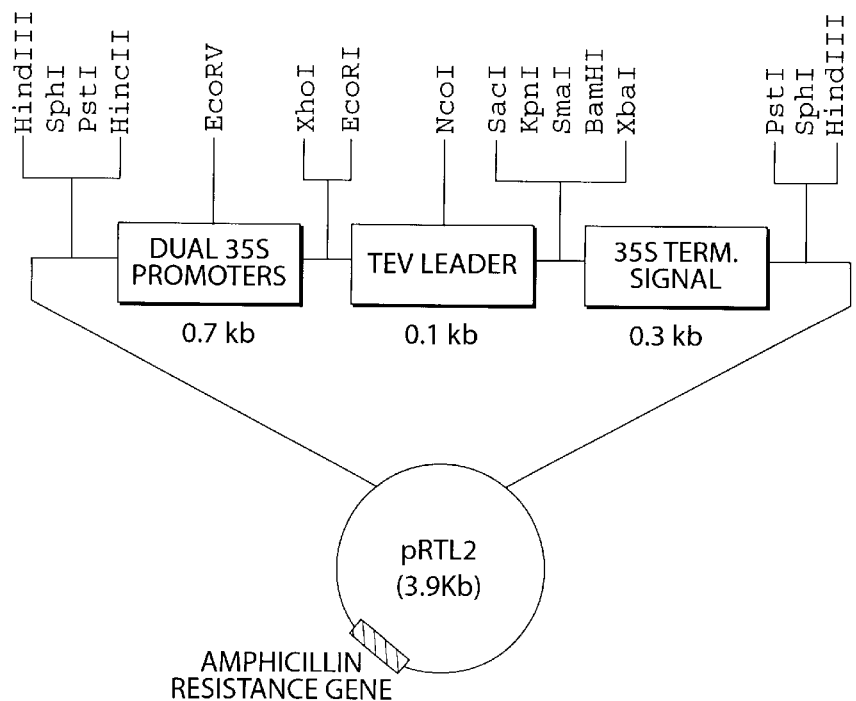
FIG. 2 is a diagrammatic plasmid construct illustrating the construction of the intermediate vector pRTL2 having the CaMV 35S dual promoters.
Figure 3A:
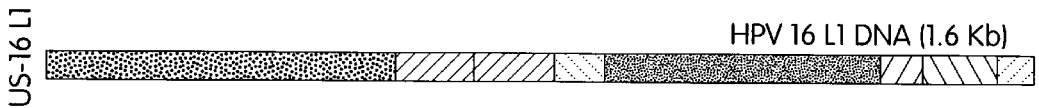
FIG. 3 is a diagrammatic plasmid construct illustrating the construction of the binary vector pUS-L series haboring the gene encoding 18-L1, 18-L2, 16-L1, or 16-L2, one of the capsid components of HPV.
Figure 3B:
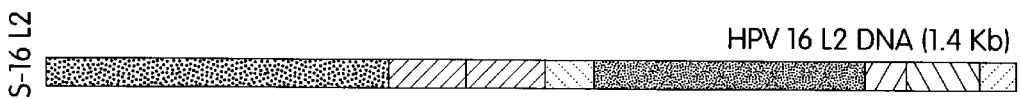
Figure 3C:
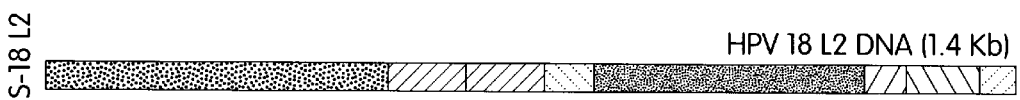
Figure 3D:
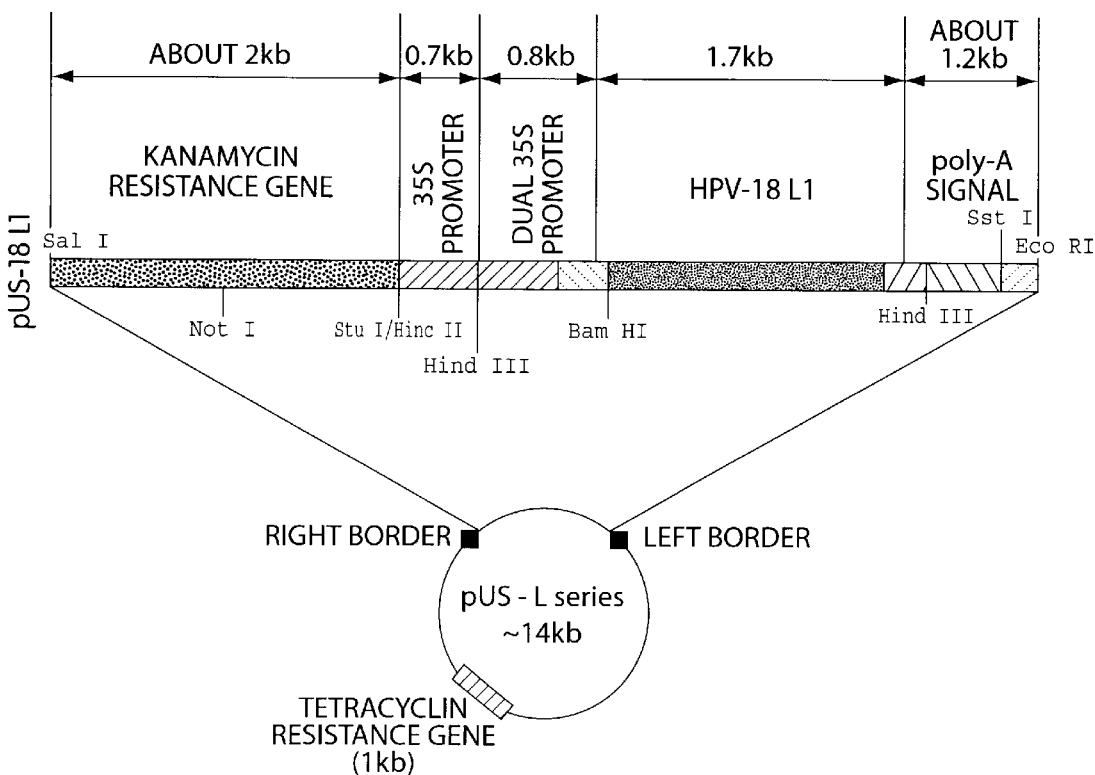

Said pRTL2 which was obtained from Dr. James Carrington of Texas A & M University comprises CaMV 35S dual promoters and TEV 5' untranslated leader sequence so that it is useful for constructing a plant expression vector, the diagrammatic structure of which is shown in FIG. 2.

Figure 1:
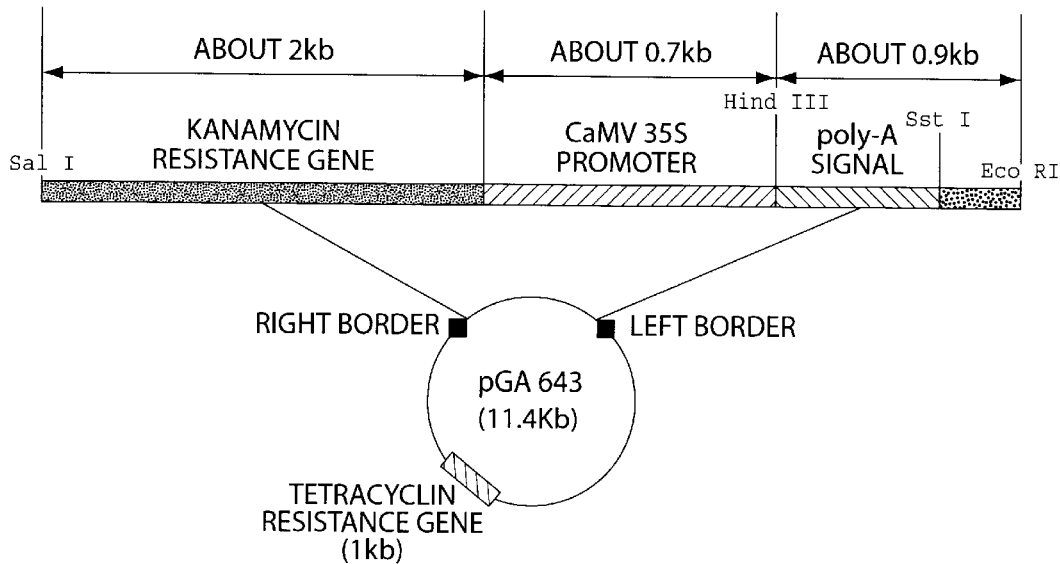
FIG. 1 is a diagrammatic plasmid construct illustrating the construction of the binary vector pGA643 used in the transformation with Agrobacterium.

B. Construction of an expression vector of a gene encoding an HPV capsid protein DNA segments of about 2.7 kb containing a gene for HPV L1, or about 2.4 kb containing a gene for HPV L2 obtained from Hind III-treated pRTL2-L series were inserted into the Hind III restriction site of pGA643 whose diagrammatic structure is shown in FIG. 1 to give the final binary vectors necessary for plant transformation. The resulting binary vectors were designated as pUS-L series and one of the vectors, pUS-18 L1 was deposited in KRIBB on Feb. 3, 2000, with the accession number of KCTC 0729BP.

Treatment of the pUS-L series with Hind III shows the existence of a gene for L1 (1.6 kb) or a gene for L2 (1.4 kb) operably linked to a 35S promoter (0.7 kb) and a TEV leader sequence (0.1 kb) in 5' terminus thereof and 35S terminal sequence (0.3 kb) in 3' terminus thereof. As a result of treating same plasmid with Sma I and Xba I, it was confirmed that the gene for L1 or L2 was duly positioned for the expression to be regulated under the control of the promoter.

Example 2
Transformation of Agrobacterium

Plasmids pUS-L series were transferred to *Agrobacterium tumefaciens* strain LBA 4404 obtained from ClonTech Laboratories, Inc. by freeze-thaw method (Holsters M., de Waele D., Depicker A., Messens E., Van Montagu M., Schell J., 1978, *Mol. Gen. Genet.* 163: 181–187).

Agrobacterium was cultured in 5 ml of YEP (yeast extract peptone broth) medium at 28° C. for 24 hours and centrifuged at 5,000 rpm at 4° C. to obtain a bacterial pellet. The pellet was resuspended in 1 ml of ice-cold 20 mM potassium chloride and 1 μg of pUS-L DNA was added to the suspen-

TABLE 1

| Target gene | Primer | Sequence |
| --- | --- | --- |
| HPV-18 | Sense | 5' ACCTCGAGCTCGGATGTGCCTGTATACA 3' |
| LI | antisense | 5' ACACACCCGGGTTACTTCCTGGCACGTA 3' |
| HPV-18 | Sense | 5' TGAGCTCAAAGTATGGTATCCCACCGTGCCGCA 3' |
| L2 | antisense | 5' CCCGGGAGGTGGAAGATATACGGTATTGTC 3' |
| HPV-16 | Sense | 5' GAGCTCCACAATATACAATTATTGCTGATG 3' |
| LI | antisense | 5' CCCGGGTCAACATACATACAATACTTACAGC 3' |
| HPV-16 | Sense | 5' GAGCTCACTTAACAATGCGACACCACAAACG 3' |
| L2 | antisense | 5' CCCGGGACAGGAGGCAAGTAGACAGTGGC 3' |

PCR buffer solution containing 10 mM Tris (pH 8.3), 50 mM potassium chloride and 0.8 mM magnesium chloride was used. PCR was carried out in a thermocycler (Perkin Elmer) under the operating condition of denaturation (94° C., 2 min), annealing (56° C., 1.5 min), and extension (72° C., 2.5 min), and further reaction in 72° C. for 10 min. The amplification cycles were repeated 30 times. The PCR products were electrophoresed and purified using Geneclean kit (BioRad, USA) to give amplified genes encoding HPVsion. The mixture was frozen in liquid nitrogen for 5 minutes, thawed in 37° C. water bath for 5 minutes, and then mixed with 1 ml of fresh YEP medium. The mixture of pUS-18 L1 and *A. tumefaciens* was then incubated at 28° C. for 2–4 hours with gentle agitating. The mixture was plated on YEP agar medium containing 300 μg/ml steptomycin and 50 μg/ml kanamycin and incubated at 28° C. for 2–3 days to select the transformed bacteria haboring one of the pUS-L series.

The plasmids pUS-L series were extracted from the obtained transformants by alkaline lysis, treated with Hind III, and separated by 1% agarose gel electrophoresis. For more accuracy, the bands of the gel were examined by hydridization with synthetic [$\alpha$-$^{32}$P] dCTP-labeled 18 L1, 18 L2, 16 L1 or 16 L2 probes because the existence of auxiliary plasmids in bacterium made a band-dragging.

As a result, the Hind III fragment haboring a gene for L1 was detected as a band in the position corresponding to 2.7 kb in size, while the fragment haboring a gene for L2 in the position corresponding to 2.4 kb in size.

Example 3

Trasformation of Plant

A. Sterilization of seeds

Fertile seeds of tobacco NC82 and tomato 'Seokwang' were soaked in 70% ethanol for 10–15 seconds with gentle agitation, immersed in 2% sodium chloride solution for 10–30 minutes, washed with distilled water 3–5 times for removing the remaining sodium chloride, and then used for sowing or transformation.

Tobacco was grown in flats under moderate light (16 hours/day), temperature of 25° C. and relative humidity of 70% for 10 weeks and the leaves in the state of 6 real leaves were used for transformation.

Tomato was grown under moderate light (16 hours/day), temperature of 27° C. and relative humidity of 70% in sterilized condition for 10 days and a seed leaf before the formation of the real leaves was used for transformation.

B. Transformation of tobacco

Leaf disc transformation was performed in accordance with the procedures of Horsch et al. (Agrobacterium-mediated leaf disc transformation, Horsch R. B., Fry J. E., Hoffman N. L., Eicholts, Rogers S. C., Fraley R. T., 1985, *Science* 227: 1229–1231).

The healthy and unblemished leaves of the young plants of which leaves are 3–5 cm long were cut into small discs of 1 cm×0.5 cm to produce wounded edges and the discs of leaves were precultured in callus-inducing media. 10 ml of the culture of transformed LBA 4404 precultured in YEP medium (pH 5.7) at 28° C. for one day was centrifuged and the pellet was resuspended in the same volume of YEP medium devoid of antibiotics. After further centrifugation, resuspension in MS medium without antibiotics was added with the precultured disc of tobacco and mixed well for 1–2 minutes. The leaf disc was dried on 3MM paper, slightly pressed on a callus-inducing agar medium with the back surface upward and cocultivated in plant tissue culture reactor maintained at 28° C. for two days. After the co-cultivation, the disc of tobacco leaf was rinsed with sterile water 3 or 4 times in order to discard the remaining bacterium, dried on a 3MM paper, and transferred to a medium containing kanamycin to select the transferred neo gene and carbenicillin to prevent the overgrowth of Agrobacterium. Callus was formed after 3 weeks from the inoculation and the developed shoots after 4 weeks were excised from the callus and transplanted to root-inducing medium supplemented with 0.05 mg/l NAA(Sigma).

C. Adjustment to soil and regeneration

Rooted plantlets were washed with sterile water and subsequently transplanted to sterile soil-pots covered with a vinyl wrap. After 1 week, the vinyl wrap was removed to regenerate a whole plant.

Through the selection based on kanamycin resistance, 13 transformants were obtained. Among the total leaf tissues, about 67% of discs thereof were differentiated into calli, 65% of the calli generated shoots and the ratio of root-forming plants was below 10 percents.

Example 4

Isolation of Genomic DNA from the Transformant

Genomic DNAs isolated from the tobacco and tomato transformants selected on the kanamycin-containing medium were tested in accordance with the protocol of southern blotting or PCR to ascertain the position of a gene for L1(or L2) of HPV-18(or HPV-16). The leaf tissue of the transgenic plant was ground into a fine powder in a liquid nitrogen with a mortar, the obtained powder was transferred to a 50 ml microfuge tube containing 5 ml of extraction buffer solution (7M urea, 0.35 M $Na_2SO_4$, 50 ml Tris (pH 8.0), 20 mM EDTA, 1% sarcosyl, 0.6% SDS) and the mixture was incubated in 60° C. water bath for 10 minutes. The mixture was added with 5 ml of phenol and mixed well for 10 minutes successively. Then, 5 ml of chloroform was added to the obtained mixture for 5 minutes to remove the phenol layer. After the mixture was centrifuged at 12,000 times gravity for 5 minutes, 5 ml of isopropyl alcohol was added to the supernatant to precipitate DNA. The DNA pellet was resuspended in 750 $\mu$l of TE buffer solution (50 mM Tris, pH 8.0, 10 mM EDTA), digested with 1.5 $\mu$l of 10 mg/ml RNase at 60° C. for 30 minutes, and then isolated by phenol extraction.

50 mg of the transformed tomato leaf selected on the medium containing kanamycin was mixed with 0.5 ml of buffer solution (50 mM Tris, pH 7.6, 100 mM NaCl, 50 mM EDTA, 0.5% SDS, 10 mM $\beta$-mercaptoethanol, 50 mg/ml RNase) and the mixture was placed at room temperature for 1–2 hours. Then, the mixture was centrifuged at 12,000 rpm for 15 minutes, treated with phenol/chloroform twice, and then treated with same volume of isopropanol at −20° C. for 30 minutes. After further centrifugation, the pellet was washed with 70% ethanol and resuspended in 30 $\mu$l of water for the spectroscopy at 260 nm.

Example 5

Total RNA Isolation from the Transgenic Plant

Total RNAs were isolated from the leaves of transgenic tobacco and tomato haboring the gene for HPV-L by tri-reagent method (Chomczynski, 1987, *Analytical Biochemistry*). 2–5 g of the leaf tissue was ground into a fine powder in liquid nitrogen, mixed with 10 ml of tri-reagent, agitated for 10 seconds, and placed on ice for 15 minutes. 2 ml of chloroform was added to the mixture, the reaction was allowed to proceed for 15 minutes, and the mixture was centrifuged at 3,000 rpm at 4° C. for 20 minutes. To the supernatant was added 10 ml of isopropanol to precipitate RNA for 10 minutes and further centrifuged at 10,000 times gravity for 20 minutes. The resulting RNA pellet was washed with 75% ethanol, resuspended in sterile, DEPC-treated water, and stored at −70° C. after the optical density was measured at 260 nm and 280 nm.

Example 6

PCR with the Leaves of Transgenic Plant

A. Identification of the gene for HPV capsid protein

Young leaf tissues were cut into 3 mm×3 mm in size, crushed in 40 $\mu$l of 0.25 M NaOH, and boiled for 30 seconds. After centrifugation at 12,000 rpm for 3 minutes, 2 $\mu$l of the supernatant was used as a PCR template. PCR was conducted under the condition of pre-denaturation at 99° C. for 5 minutes and 30 cycles of template denaturation (94° C., 1.5 minutes), primer annealing (58° C., 1.5 minutes), and extension by polymerase (72° C., 2.5 minutes). As PCR primers, synthetic oligonucleotides listed in the above table 1 were used. The PCR products were isolated and analyzed by 1.2% agarose gel electrophoresis. As a result of the PCR wherein the solution of the ground shoot of the transgenic tobacco was used as a template, a gene encoding L1 was detected in the position corresponding to 1.7 kb in size by southern blotting (see FIG. 4). By the same protocol, genes encoding HPV-16 L1, HPV-16 L2 and HPV-18 L2 were analyzed, respectively.

B. Genomic PCR

As a template, 1 µg of genomic DNA isolated in Example 4 was used. PCR condition comprised pre-denaturation at 98° C. for 2 minutes and 30 cycles of template denaturation (94° C., 1.5 minutes), primer annealing (53° C., 1.5 minutes) and extension by polymerase (72° C., 2.5 minutes), and further reaction at 72° C. for 10 minutes. Genomic DNA was isolated from the leaves of 8 transgenic tomatoes. The results of the electrophoresis of the PCR products showed the dragging of the band apart from the expected position. Hydridization using [α-$^{32}$P] dCTP-labeled L1 or L2 as a probe revealed that the gene encoding HPV capsid protein was inserted into the tomato genome properly.

C. Reverse transcription polymerase chain reaction (RT-PCR)

In order to confirm that the inserted gene was properly transcribed into mRNA, RT-PCR was conducted with the total RNAs isolated from the transgenic tobacco. The first DNA strand was synthesized at 37° C. by reverse transcriptase of moloney murine leukemia virus (MMLV) in the reaction solution containing 100 mM Tris-HCl, 50 mM KCl, 5 mM MgCl$_2$ and 1 mM dNTP, using 1 µg of RNA isolated in Example 5 as a template. The reverse transcriptase was inactivated at 99° C. for 5 minutes, and then PCR was performed under the condition of pre-denaturation at 94° C. for 2 minutes in 200 µl of the PCR buffer solution (2 mM MgCl$_2$, 10 mM Tris, pH 8.3, 50 mM KCl) containing 0.6 µM of oligonucleotides of SEQ ID NO:1 and SEQ ID NO:2 as primers. The cycle of denaturation (94° C., 1.5 minutes)-annealing (57° C., 1.5 minutes)-extension (72° C., 2.5 minutes) was repeated 25 times and the amplified DNA fragments corresponding to the gene for L1, the size of which is 1.7 kb, were separated by 1.2% agarose gel electrophoresis. Through the same method, the expression of the gene for L2 was detected and the size of the amplified gene by RT-PCR was 1.4 kb (see FIG. 5).

Example 7

Southern Blotting

PCR products digested with restriction enzymes were separated on the basis of fragment length on a 1% agarose gel. The gel was denatured in 1.5 M NaCl followed by 0.5 N NaOH, washed with distilled water, and equilibrated. The fragments were, then, blotted onto the nylon membrane (Hybond-N, Amersham) which was previously soaked in 10×SSC for more than 5 minutes, by capillary action for 12–16 hours. Remaining agarose was washed with 6×SSC for 5 minutes and the DNA fragments were fixed to the membrane by ultraviolet cross-linking (254 nm, 0.18 J/Sq·cm$^2$) or oven baking at 80° C. The pre-hybridization and hybridization reaction were carried out according to the established protocol which is described below in detail.

Example 8

Northern Blotting

A. Method

30 µg of total RNA isolated in Example 5 was concentrated to the final volume of 4.5 µl. 10×MOPS (0.2 M 3-(N-morpholino) propanesulfonic acid, pH 7.0, 50 mM sodium acetate, 10 mM EDTA, pH 8.0), formamide and formaldehyde were added to the RNA solution in the ratio of 1:1.8:5 to the final volume of 20 µl. The secondary structure of the RNA was denatured into a single-stranded state by heating at 65° C. for 15 minutes. Then, the RNA was electrophresed on 1% agarose gel containing 2.2 M formaldehyde at voltage of 4 V/cm using 2 µl of formaldehyde gel loading buffer solution (50% glycerol, 1 mM EDTA, pH 8.0, 0.25% bromophenol blue, 0.25% xylene cyanol FF).

Formaldehyde was then washed with DEPC-treated water for 1 hour and the RNA fragments were transferred onto nylon membrane (Hybond-N, Amersham) by capillary action for about 16 hours. After transfer, RNA was fixed to the membrane by ultraviolet cross-linking (254 nm, 0.18 J/Sq·cm$^2$) and by oven baking at 80° C. for 1 hour.

L1 and L2 PCR products amplified with HPV-18 or HPV-16 were labeled with [α-$^{32}$P] dCTP using a random primer labeling kit (Boeringer Manheim) and separated by sephadex G-50 column chromatography. The nylon membrane covalently bound with RNA was treated with 6 ml of pre-hybridization solution (5×SSC, 5×Denhardt's reagent, 0.1% SDS, 100 µg/ml denatured salmon sperm DNA), placed in hybridization reaction oven of 65° C. for 2 hours, and hydridized with radiolabeled DNA which was previously denatured in boiled water for 5 min for 18 hours.

After the hybridization reaction, the membrane was washed with 2×SSC and 0.1% SDS at room temperature for 10 minutes, which was followed by washing with 0.2×SSC and 0.1% SDS at 42° C. for 20 minutes, while the temperature was increased up to 65° C. in accordance with the signal detected by Geiger counter to remove unbound radioactivity. The regions of hydridization were detected autoradiographically by placing the membrane in contact with X-ray film at −70° C.

B. Analytical results in transgenic tobacco

In order to get more apparent proofs that the gene encoding L1 or L2 inserted into the genome of the tobacco could be transcribed into mRNA even in the second generation, northern blot was carried out with the total RNA of leaf, stem, and root, respectively. Northern blot revealed that the gene for L1 was expressed in all the tissue of the second generation of the transgenic plant. Further, a signal at the 1.7 kb position corresponding to the size of the open reading frame of L1 was detected and other small transcripts such as about 3 kb or smaller than 1.7 kb in size were observed. The transgenic tobacco #1 expressed more amount of L1 in leaf tissue than in stem or root tissue whereas the transgenic tobacco #2 more in root tissue than in the rest. This difference between the transcription levels of each of transgenic plants was supposed to be based on the insertion site of exogenous DNA and the copy number.

C. Analytical results in transgenic tomato

RNAs isolated from 8 plants showing the amplification of gene encoding L1 or L2 by southern blot were analyzed by northern blot. 30 µg of total RNA was electrophoresed on 1% agarose gel containing formaldehyde followed by fixation onto nylon membrane, and hybridization reaction gave result in transcription signal at the position of about 2.0 kb in size. The size representing 1.7 kb of a gene for L1 plus about 0.14 kb of TEV 5' untranslated sequence and about 0.2 kb of polyadenylation tail, which was detected by comparison with the position of rRNA.

All tested plants except only one showed the L1 transcription signal, which could be clearly detected even though the levels thereof were slightly different from one another. Most of all, the gene encoding HPV-18 (or -16) L1 (or L2) was under the control of 35S dual promoters successfully (see FIG. 6).

Example 9
Selection of the Second Generation of Transgenic Plants Based on Kanamycin Resistance The segregation pattern was investigated by selection of the transformed tobacco having kanamycin resistance after the seeds of the second generation ($T_2$) of the transgenic plant haboring the gene encoding HPV-L series have been grown in the medium containing 500 mg/l of kanamycin.

$T_2$ seeds were induced to germinate in kanamycin-containing medium. After 2 weeks, it was observed that the non-transformed tobacco was browned and blighted three weeks after germination.

By the same method, the second generation of the transformed tomato was selected in medium containing 50 mg/l of kanamycin.

Example 10
Cesium Chloride Density Gradient Analysis of Virus Like Particles Produced in Transgenic Plant HPV-L series proteins can form the virus like particles by self-assembly. In order to separate these VLPs, 5g of the leaves of the transgenic plants was frozen in liquid nitrogen and ground into a powder with a cold mortar. The powder was resuspended in 25 ml of buffer solution (20 mM sodium phosphate, pH 7.0, 0.15 M NaCl, 20 mM sodium ascorbate, 0.1% Triton X-100, 0.5 mM PMSF) and centrifuged at 1,000 times gravity for 15 minutes. The supernatant was collected and further ultra-centrifuged at 100,000 times gravity for 1.5 hours, the pellet was resuspended in 5 ml of buffer solution A (1 mM $MgCl_2$, 1 mM $CaCl_2$, 1 mM PMSF in PBS), and 5.2 g of cesium chloride was added to the solution followed by addition of buffer solution A to the final volume of 13 ml.

After the ultracentrifugation at 100,000 times gravity for 22 hours, the existence of VLP was confirmed by measuring the optical density at 280 nm and via transmission electron microscopy of the each fraction fractionated on the base of the density (see FIG. 7).

The size of VLPs measured by TEM was about 20–30 nm and the particles were aggregated in the fraction of about 1.30 g/ml density.

Example 11
Analysis of Protein by SDS-PAGE and Western Blot

25 $\mu$l of the obtained fraction of protein was mixed with 5 $\mu$l of a 6×SDS buffer solution (0.35 M Tris-Cl, pH 6.8, 10% SDS, 30% glycerol, 9.3% DDT), boiled at 100° C. for 5 minutes, and electrophoresed on 10% polyacrylamide gel at voltage of 25 mA. After the marker dyes reached the bottom of the gel, the gel was silver stained to develop the band of protein.

The protein of a separating gel was transferred onto a nitrocellulose membrane and the background of nonspecific binding sites was blocked with skim milk (3% skim milk in PBS) for 1.5 hours. The protein bound membrane was washed with a PBST buffer solution (1% Triton X-100 in PBS) and allowed to react with the primary antibody against HPV-L series proteins, which was previously diluted with the blocking solution (1:2500) for 2 hours.

Following the washing of the membrane with PBST (1% Triton X-100 in PBS), the conjugate of immunoglobulin G and horseradish peroxidase which was diluted with the blocking solution (1:3,000) was reacted with the primary antibody bound to the protein at room temperature for 50 minutes.

After washing with PBST (1% Triton X-100 in PBS), the membrane was reacted with ECL (enhanced chemiluminescence) solution, and placed in contact with an X-ray film to detect the antigen-specific proteins.

The VLP protein band in the position of 55 kDa was shown in the silver-stained gel after the VLP fraction obtained by CsCl density gradient was electrophoresed by SDS-PAGE.

By the western blot analysis, it was assured that the fraction corresponding to the density between 1.28 g/ml and 1.35 g/ml had antigenic proteins which could bind to the HPV-specific antibodies, i.e., HPV virus like particles.

Example 12
Test for Antigenicity of HPV Like Particles by Oral Administration A. Oral administration of HPV like particles and collection of the samples VLPs of the fraction detected by TEM were harvested, the proteins of 30 kDa or less in size and CsCl were removed by Centricon-30, and then quantitated by Bradford method. Balb/c mice of 8 weeks were orally administered with said VLPs for about 11 weeks four times on $1^{st}$, $2^{nd}$, $17^{th}$ and $29^{th}$ day. Then, 200 $\mu$l of blood was collected from the heart by syringe on 0, $10^{th}$, $18^{th}$, $29^{th}$, $37^{th}$ and $76^{th}$ day, respectively, for detecting the production of immunoglobulin G. The collected blood was incubated at 37° C. for 1 hour and then 4° C. for 5 minutes. The serum was harvested by centrifugation at 10,000 times gravity.

In the meantime, the feces were collected on 0, $10^{th}$ and $21^{st}$ day, respectively, for detecting the production of immunoglobulin A. 1 ml of PBS (1% BSA, 1 mM PMSF) was added to 0.1 g of feces and the mixture was placed at 4° C. overnight. The mixture was then homogenized, centrifuged at 10,000 times gravity, and the supernatant was stored at −20° C.

B. Enhanced chemiluminescence Enzyme-linked immunosorbent assay (ECL-ELISA)

ECL-ELISA (BioTechnique 22: 278–280, 1997) is a powerful method of which the sensitivity is 20 times higher than that of the conventional ELISA method in measuring the ability to induce the production of antibodies. The antibodies were assayed by the ECL-ELISA kit purchased from Amersham (England) under the manufacturer's instruction.

Antigenic protein was diluted with PBS and bonded to an EIISA plate at 4° C. overnight. The wells were washed with PBST (1% Triton in PBS) and blocked with 5% PBSA (5% BSA in PBS). After further washing the wells with PBST twice, the antigen in each well was allowed to react with a serum diluted in 3% PBSA at room temperature for 2 hours. The well was washed again with PBST twice and added with IgG-horseradish peroxidase conjugate diluted in 3% PBSA (1:1,000) at room temperature for 1.5 hours. The well was washed with PBST twice, supplemented with ECL solution A and B, and allowed to react with the reagents for 5 minutes. After the plate was exposed to a film for the detection of radioactivity, the radioactivity levels were measured using MacBAS2000 (Fuji, Japan).

ECL-ELISA for detecting IgA was performed by the protocol same as aforementioned except the fact that the extract of the feces was linked with the antigen bonded plate without dilution and that horseradish peroxidase-conjugated IgA was used as a secondary antibody. All the process of ECL-ELISA was repeated three times.

According to the results of ECL-ELISA described in FIG. 8 and FIG. 9, oral administration of the antigenic HPV like particle produced in the transgenic plants of the invention elicits the mucosal immunity, which was proven by the increment of IgA level after the oral administration, as well as the systemic immunity proven by the IgG production even though the levels of IgG when orally administered were much lower than those when intraperitoneally injected.

c. Oral administration of the HPV like particles through consumption of the transgenic plant Mice were fed with the fruit of the transgenic tomato three times a day for three weeks in the amount of 5 g per each intake. Then the activity of the transgenic plants to elicit the antibody production was measured by the same method as described above. The results ascertains that not only the purified HPV like particles but also the transgenic plant itself may be used as an oral vaccine which can induce the production of systemic antibodies (IgG) as well as mucosal antibodies (IgA).

Example 13

Test for Antigenicity of HPV Like Particles by Intraperitoneal Injection

White mice ICR of 14 weeks were injected intraperitoneally with the antigenic HPV like particles produced in the transgenic plant of the invention, alone or in combination with incomplete Freund's adjuvant, 21 times on the $7^{th}$ and $21^{st}$ day respectively and then the blood was collected from the heart by syringe on 0, $13^{th}$, $22^{nd}$, $30^{th}$, $37^{th}$, $49^{th}$ and $69^{th}$ day.

The level of antibodies produced was measured by ECL-ELISA according to the protocol described in Example 12. The result shows that IgG level was increased dramatically after 2 weeks from the injection while the injection in the combination with the incomplete Freund's adjuvant was efficient in inducing the antibody production 1.5 times more than the injection of the protein alone (see FIG. 10).

The foregoing description of the invention has been directed to a particular preferred embodiment in accordance with the requirements of the patent and statutes and for purpose of explanation and illustration. It will become apparent to those of skilled in the art that modifications and changes may be made without departing from the scope and the spirit of the invention.

Industrial Applicability

The transgenic plant of the present invention and a part, seed, fruit and the progenies thereof are useful in preparation of prophylactic or therapeutic vaccines. Since the HPV like particles can be produced and purified in the transgenic plants of the present invention massively and economically with the antigenicity maintained effectively, they can be used in the development of vaccine, especially for the cancer of cervix, of therapeutic or diagnostic kits, and of medicines as well as in screening the antibodies against HPV and novel material which has therapeutic activity for HPV-related diseases.

More preferably, the transgenic plants of the present invention can be used as an oral vaccine which has advantages such as convenience of administration and no need for purification or specialized technique for administration.

What is claimed is:

1. A transgenic plant comprising a DNA sequence encoding a human papillomavirus (HPV) capsid protein, wherein said plant assembles the HPV capsid protein into antigenic HPV like particles.

2. The transgenic plant according to claim 1, wherein the DNA sequence encoding an HPV capsid protein is selected from the group consisting of a gene for HPV 16 L1, a gene for HPV 16 L2, a gene for HPV 18 L1 and a gene for HPV 18 L2.

3. A prophylactic or therapeutic vaccine comprising HPV like particles, wherein the vaccine is produced as a pharmaceutically active ingredient by a method for producing an antigenic composition containing HPV like particles comprising the steps of:

1) constructing a plasmid vector comprising a DNA sequence encoding an HPV capsid protein operably linked to a plant-specific promoter and a gene encoding a selection marker;

2) transforming a plant cell or tissue with the plasmid vector of step 1;

3) inducing a callus formation from the transformed plant cell or tissue of step 2;

4) inducing a root formation in root-inducing medium, adjusting to soil, and regenerating a transgenic plant; and 5) recovering HPV like particles from the transgenic plant.

4. The prophylactic or therapeutic vaccine according to claim 3, wherein the HPV like particles are provided in the form of the transgenic plant itself, a part of the plant, fruit, seed or extract thereof.

5. The prophylactic or therapeutic vaccine according to claim 3, wherein the vaccine is orally administrated for induction of an immune response.

6. The prophylactic or therapeutic vaccine according to claim 3, wherein the HPV like particles are administrated in the form of food containing the extract of the transgenic plants.

7. The prophylactic or therapeutic vaccine according to claim 3, wherein the vaccine is administrated in the form of an injectable solution, a spray or a patch.

* * * * *

SEQUENCE LISTING

```
<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: sense
      primer for PCR of HPV-18 L1

<400> SEQUENCE: 1
acctcgagct cggatgtgcc tgtataca                                      28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Antisense
      primer for PCR of HPV-18 L1

<400> SEQUENCE: 2
acacacccgg gttacttcct ggcacgta                                      28

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Sense
      primer for PCR of HPV-18 L2

<400> SEQUENCE: 3
tgagctcaaa gtatggtatc ccaccgtgcc gca                                33
```

```
<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Antisense
      primer for PCR of HPV-18 L2

<400> SEQUENCE: 4
cccgggaggt ggaagatata cggtattgtc                                      30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Sense
      primer for PCR of HPV-16 L1

<400> SEQUENCE: 5
gagctccaca atatacaatt attgctgatg                                      30

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Antisense
      primer for PCR of HPV-16 L1

<400> SEQUENCE: 6
cccgggtcaa catacataca atacttacag c                                    31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Sense
      primer for PCR of HPV-16 L2

<400> SEQUENCE: 7
gagctcactt aacaatgcga caccacaaac g                                    31

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Antisense
      primer for PCR of HPV-16 L2

<400> SEQUENCE: 8
cccgggacag gaggcaagta gacagtggc                                       29
```